US00PP35889P2

(12) United States Plant Patent
Kim

(10) Patent No.: US PP35,889 P2
(45) Date of Patent: Jun. 25, 2024

(54) ***SCABIOSA* PLANT NAMED 'SCBE01'**

(50) Latin Name: *Scabiosa columbaria x japonica*
Varietal Denomination: SCBE01

(71) Applicant: Seoha Plant Breeding Institute, Gyeonggi-do (SK)

(72) Inventor: Kyung-Sook Kim, Gwangju (SK)

(73) Assignee: Seoha Plant Breeding Institute (KR)

( * ) Notice: Subject to any disclaimer, the term of this patent is extended or adjusted under 35 U.S.C. 154(b) by 0 days.

(21) Appl. No.: 18/142,655

(22) Filed: May 3, 2023

(51) Int. Cl.
*A01H 5/02* (2018.01)
*A01H 6/00* (2018.01)

(52) U.S. Cl.
USPC ..... Plt./478

(58) Field of Classification Search
USPC ..... Plt./263.1, 478
See application file for complete search history.

(56) References Cited

PUBLICATIONS

CPVO Register. citation for 'SCBE01'. https://online.plantvarieties.eu/publicConsultationDetails?registerId=20222188&denomination=scbe01&order=denomination&reverse=true. 2 pages (Year: 2022).*

* cited by examiner

*Primary Examiner* — Karen M Redden
(74) *Attorney, Agent, or Firm* — Cassandra Bright

(57) ABSTRACT

A new and distinct cultivar of *Scabiosa* plant named 'SCBE01' is disclosed, characterized by floriferous plants with very low, compact habits, and vigorous growth. The new variety is a *Scabiosa*, suitable for outdoor garden and container uses.

3 Drawing Sheets

Latin name of the genus and species: *Scabiosa columbaria* x *japonica*.

Variety denomination: 'SCBE01'.

BACKGROUND OF THE INVENTION

The new *Scabiosa* cultivar is a product of a planned breeding program conducted by the inventor. The objective of the breeding program was to produce floriferous new *Scabiosa* varieties with low, mounding habits. The crossing resulting in this new variety was made during 2013, at a nursery in Gwangju-si, South Korea.

The seed parent is an unpatented, propriety variety of *Scabiosa columbaria*. The pollen parent is an unpatented, propriety variety of *Scabiosa japonica*. The new variety was discovered in 2015 by the inventor in a group of seedlings resulting from the 2013 crossing, at the same nursery in Gwangju-si, South Korea.

Asexual reproduction of the new cultivar 'SCBE01' was first performed by vegetative cuttings during 2013, in Gwangju-si, South Korea. Subsequent propagation has shown that the unique features of this cultivar are stable and reproduced true to type in multiple successive generations.

SUMMARY OF THE INVENTION

The cultivar 'SCBE01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SCBE01'.

These characteristics in combination distinguish 'SCBE01' as a new and distinct *Scabiosa* cultivar:

1. Very low, compact plant (groundcover), no growth regulators needed.
2. Floriferous; one plant produces over 50 flowers.
3. Rapid, vigorous growth.

PARENT COMPARISON

Plants of the new cultivar 'SCBE01' are similar to plants of the seed parent, in most horticultural characteristics, however, plants of the new cultivar 'SCBE01' differ in the following;

1. Plants of the new variety are not as tall as plants of the seed parent.
2. The new variety produces more flowers and flower stems than the seed parent.
3. Flowers of the new variety are smaller than flowers of the seed parent.

Plants of the new cultivar 'SCBE01' are similar to plants of the pollen parent, in most horticultural characteristics, however, plants of the new cultivar 'SCBE01' differ in the following;

1. Plants of the new variety are smaller than plants of the pollen parent.
2. The new variety produces more flowers and flower stems than the pollen parent.
3. The new variety grows faster than the pollen parent.

COMMERCIAL COMPARISON

Plants of the new cultivar 'SCBE01' can be compared to the commercial variety *Scabiosa* 'Butterfly Blue', unpatented. These varieties are similar in most horticultural characteristics; however, 'SCBE01' differs in the following:

1. Plants of the new variety are not as tall as plants of this comparator.
2. Flower stems of the new variety are stronger than flower stems of this comparator.
3. Flowers of the new variety are smaller than flowers of this comparator.
4. The new variety produces more flowers than this comparator.

BRIEF DESCRIPTION OF THE PHOTOGRAPHS

The accompanying photograph in FIG. 1 illustrates in full color a typical plant of 'SCBE01' grown in a greenhouse in Waddinxveen, The Netherlands.

Figure 1:
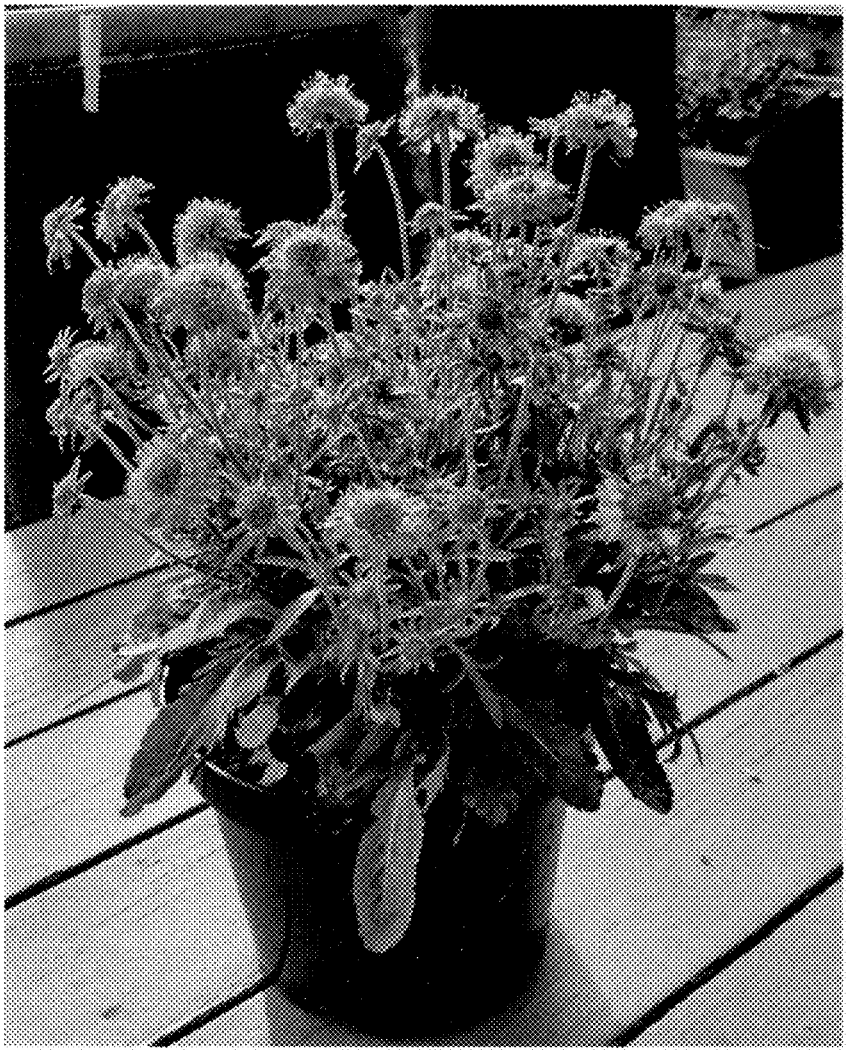
Figure 2:
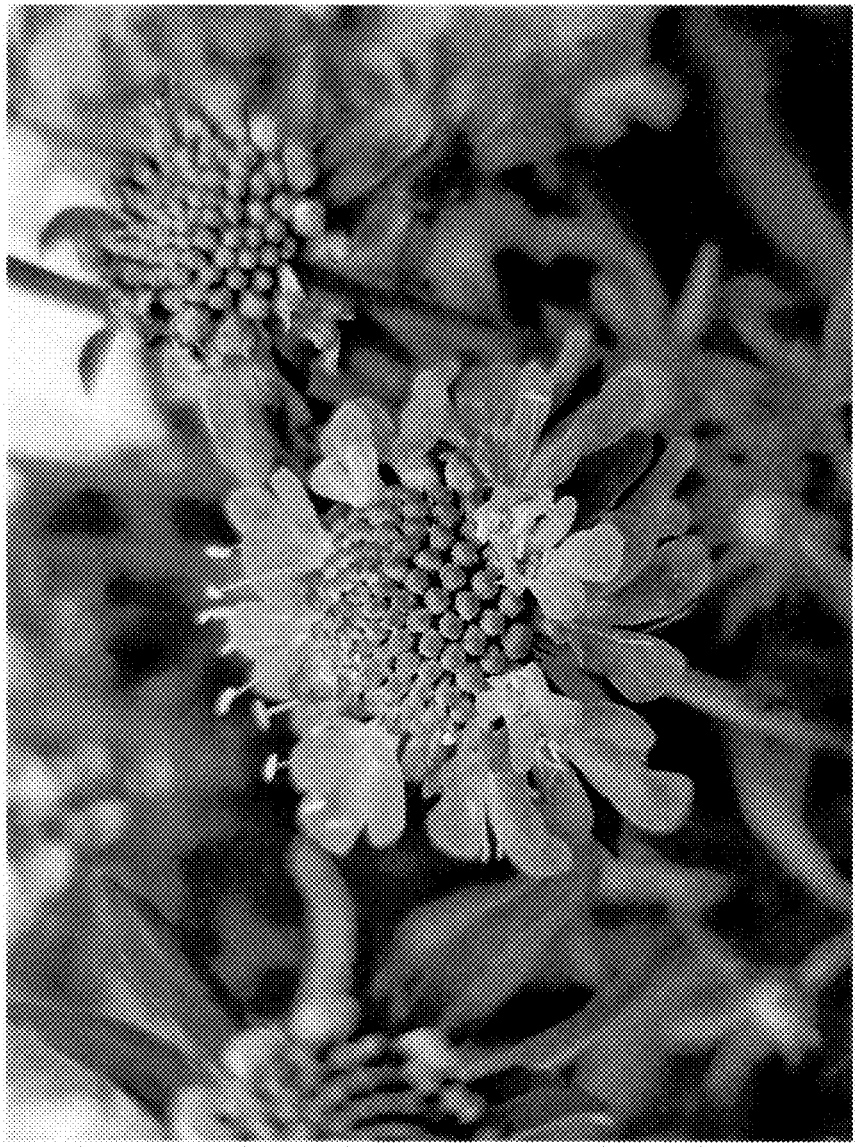
FIG. 2 illustrates in full color a typical inflorescence of 'SCBE01'.
Figure 3:
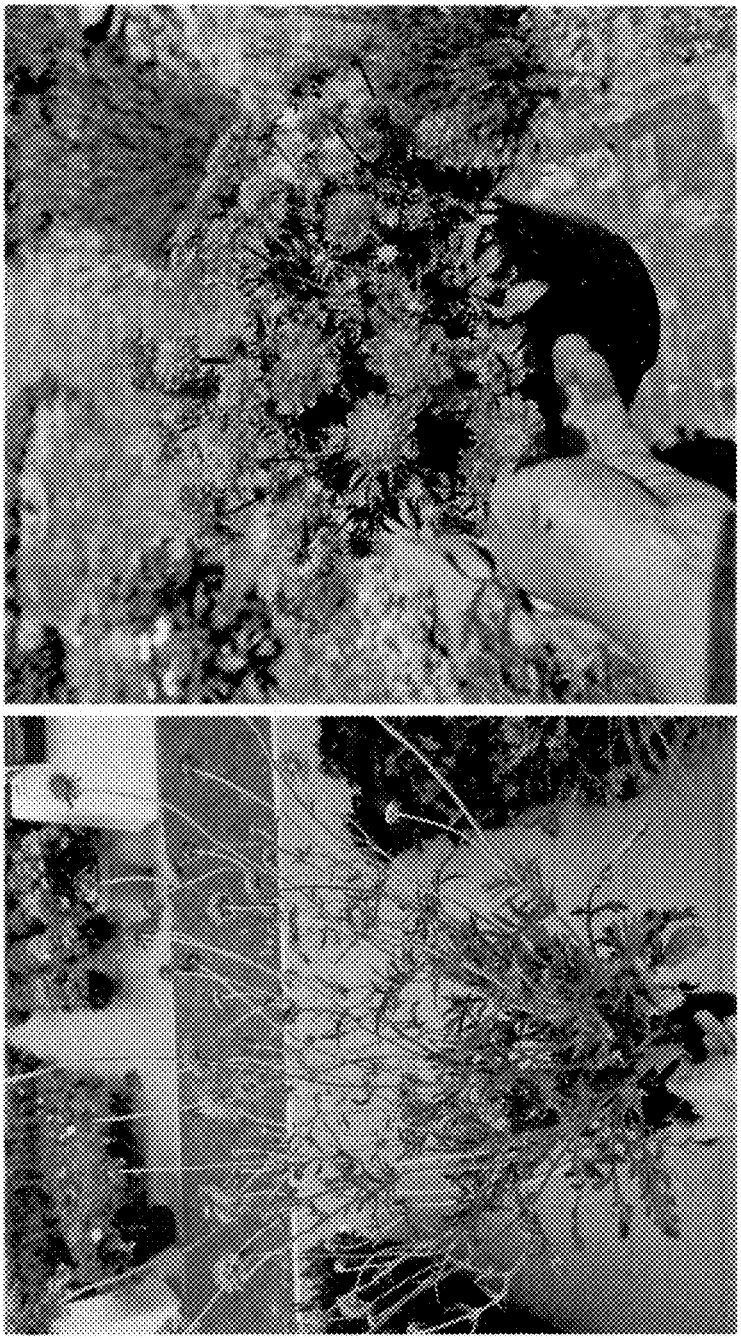
FIG. 3 illustrates a comparison of the new variety (right wide of photo) and the well known comparator 'Butterfly Blue'.

Photos are of plants of approximately 9 months of age. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'SCBE01' plants grown in a greenhouse in Waddinxveen, The Netherlands, under natural lighting. Measurements were taken during April of 2016. The plants were approximately 18 weeks old. The growing temperature ranged from approximately 12° C. to 35° C. during the days, 4° C. to 28° C. during the nights. Measurements and numerical values represent averages of typical plant types.

Botanical classification: *Scabiosa columbaria* x *japonica* 'SCBE01'.

PROPAGATION

Time to initiate rooting: 6 weeks in spring/summer.
Time to rooted plant: 12 weeks in spring/summer.
Root description: Fine, fibrous.

PLANT

Plant type: Herbaceous perennial.
Growth habit: Low, mounded.
Height: 12 to 15 cm.
Plant spread: 30 cm.
Growth rate: Vigorous.
Stem:
- *Branching*.—Basal rosette.
- *Quantity*.—5 main branches; 2 to 3 lateral branches per main branch.
- *Length*.—Average 3.5 cm up to peduncle.
- *Diameter*.—3 cm.
- *Shape*.—Cylindrical.
- *Color*.—RHS Yellow-Green 146C, Purple N77A at the base.
- *Texture*.—Pubescent.
- *Strength*.—Strong.

Internode Length: Up to 2.2 cm.

FOLIAGE

Leaf:
- *Arrangement*.—Opposite.
- *Attachment*.—Sessile.
- *Quantity per main stem*.—Average 12.
- *Length*.—Upper: Up to 7 cm. Lower: 8.5 cm.
- *Width*.—Upper: Up to 4.2 cm. Lower: 2.8 cm.
- *Shape*.—Upper: Pinnately lobed, oblong. Lower: Obovate.
- *Apex*.—Upper: Narrowly acute. Lower: Broadly acute to obtuse.
- *Base*.—Attenuate.
- *Margin*.—Upper: Deeply divided, entire. Lower: Serrate, lobed.
- *Texture*.—Slightly pubescent.
- *Color*.—Upper side: RHS Green 137B-C. Under side: RHS Green 137D.
- *Venation*.—Type: Pinnate. Color, upper side: RHS Green 138B-C (mid-rib, the rest not clearly visible). Color, under side: RHS Green 138C.

FLOWER

Natural flowering season: April through July.
Flower/inflorescence type: Terminal flat heads with outer and inner florets.
Quantity of flowers per plant: Approximately 30.
Flower arrangement: Asymmetric outer florets with narrow tube expanding into 2 lips — an upper lip with 3 large lobes, and lower lip with 2 or 3 smaller lower lobes.
Flower size:
- *Diameter*.—2.6 cm.
- *Depth*.—About 1.5 cm.

Persistence: Persistent.
Fragrance: None.
Inflorescence:
- *Diameter*.—Approximately 3 cm.
- *Depth*.—Approximately 1.4 cm.

Bud:
- *Shape*.—Obovate.
- *Length*.—4 mm.
- *Diameter*.—2 mm.
- *Color*.—RHS Yellow-Green 145A. More mature buds have faded Purple 77B at the top.

Outer florets:
- *Quantity*.—Average 9.
- *Diameter*.—Typical largest 9 mm.
- *Sepals*.—Quantity: 5. Shape: Linear. Margin: Entire. Apex: Acute. Length: 2 mm. Width: 0.5 mm. Color: RHS Purple N77A.
- *Lobes*.—Quantity: 5 (3 large upper lobes, 2 lower lobes). Fused or Free: Lobes join at base in a tube. Margin: Wavy. Surface: Smooth.
- *Tube*.—Length: 3 to 4 mm. Diameter: 1 to 1.5 mm. Pubescence: None visible. Color: RHS White N155D.
- *Upper lip*.—Length: About 7 mm (central lobe 7 mm; lateral lobes 5.5 mm). Width: About 1 cm (central lobe 4.5 mm; lateral lobes 3 mm). Color: Upper surface: RHS Violet 86C. Lower surface: RHS Violet N88D.

*Lower lip*.—Length: 2 mm. Width: 2 mm. Shape: Rounded. Color: Upper surface: RHS Violet 86C. Lower surface: RHS Violet N88D.

Inner florets:

*Quantity*.—About 38.

*Sepals*.—Quantity: 5. Shape: Linear. Margin: Entire. Apex: Acute. Length: 2 mm. Width: Less than 0.5 mm. Color: RHS Purple N77A.

*Corolla*.—Shape: Narrow corolla tube expanding into 2 lips, the upper with 3 lobes and the lower with 2 smaller lobes, all more or less the same size. Petal Quantity: 5 (3 large upper lobes, 2 lower lobes). Fused or Free: Fused. Diameter: About 2.5 mm. Tube Length: 2 mm. Tube Width: 1 to 1.5 mm. Lobe Margin: Entire. Lobe Surface: Smooth. Tube Color: RHS White N155D.

*Upper lip*.—Shape: 3 oblong lobes. Length: Central: 1.5 to 2 mm. Lateral: 1 mm. Width: Central: 1 mm. Lateral: 1 mm. Color: RHS Violet N82C.

*Lower lip*.—Length: Less than 1 mm. Width: Less than 1 mm. Shape: 2 rounded lobes. Color: RHS Violet N82D.

Involucral bracts:

*Quantity*.—Average 11.

*Arrangement*.—Whorl.

*Shape*.—Linear.

*Length*.—8 mm.

*Width*.—2 mm.

*Apex*.—Acute.

*Texture*.—Upper surface: Pubescent. Lower surface: Slightly pubescent.

*Color*.—RHS Green 137C; base Yellow-Green 145C.

Peduncle:

*Shape*.—Round.

*Length*.—2 to 10 cm.

*Diameter*.—1 mm.

*Texture*.—Pubescent.

*Color*.—Near RHS Yellow-Green 146C.

*Strength*.—Strong.

REPRODUCTIVE ORGANS

Outer floret:

Stamens:

*Number*.—4.

*Filament length*.—Approximately 4 mm.

*Filament width*.—Approximately 0.5 mm.

*Filament color*.—RHS White N155D.

Anthers:

*Length*.—Approximately 1 mm.

*Width*.—Approximately 0.5 mm.

*Pollen color*.—RHS White N155D.

Pistil:

*Number*.—1.

*Style*.—Shape: Linear. Size: Approximately 0.5 mm. Color: RHS White N155D at base, blending to Violet 86C.

*Stigma*.—Shape: Capitate. Size: Approximately 0.5 mm. Color: RHS Violet 77A.

*Ovary*.—Shape: Cylindrical. Size: About 1 mm or smaller. Color: RHS Yellow-Green 145A.

Inner floret:

Stamens:

*Number*.—4.

*Filament length*.—Approximately 3 mm.

*Filament width*.—Less than 0.5 mm.

*Filament color*.—RHS White N155D.

Anthers:

*Length*.—1 mm.

*Width*.—Less than 0.5 mm.

*Color*.—RHS Violet 76B.

*Pollen*.—Not observed.

Pistil:

Number.—1.

*Style*.—Shape: Linear. Size: About 1.5 mm. Color: RHS White N155D at base, blending to Violet 86C.

*Stigma*.—Shape: Capitate. Size: Less than 0.5 mm in width and length. Color: RHS Violet 77A.

*Ovary*.—Size: Less than 0.5 mm. Color: RHS Yellow-Green 145C.

OTHER CHARACTERISTICS

Seeds and fruits: Not observed.

Disease/pest resistance: Neither resistant nor susceptibility to normal diseases and pests of *Scabiosa* has been observed.

Temperature tolerance: Cold hardy to −20° C.

What is claimed is:

1. A new and distinct cultivar of *Scabiosa* plant named 'SCBE01' as herein illustrated and described.

* * * * *